United States Patent
Merrill et al.

[11] Patent Number: 6,057,485
[45] Date of Patent: May 2, 2000

[54] GAS PHASE ALKYLATION WITH SPLIT LOAD OF CATALYST

[75] Inventors: James T. Merrill, Katy; James R. Butler; Ashim Kumar Ghosh, both of Houston, all of Tex.

[73] Assignee: Fina Technology, Inc., Dallas, Tex.

[21] Appl. No.: 09/193,310

[22] Filed: Nov. 17, 1998

[51] Int. Cl.[7] .............................. C07C 1/00; C07C 2/64; C07C 2/68
[52] U.S. Cl. .................... 585/449; 585/467; 585/323
[58] Field of Search ..................... 585/467, 450, 585/449, 323

[56] References Cited

U.S. PATENT DOCUMENTS

| | | | |
|---|---|---|---|
| 4,107,224 | 8/1978 | Dwyer | 260/671 R |
| 4,169,111 | 9/1979 | Wight | 585/323 |
| 4,185,040 | 1/1980 | Ward et al. | 585/467 |
| 4,284,529 | 8/1981 | Shihabi | 582/455 Z |
| 4,489,214 | 12/1984 | Butler et al. | 585/467 |
| 4,520,220 | 5/1985 | Watson et al. | 585/467 |
| 4,559,314 | 12/1985 | Shihabi | 502/71 |
| 4,599,473 | 7/1986 | Debras et al. | 585/467 |
| 4,772,456 | 9/1988 | DeClippeleir et al. | 423/328 |
| 4,774,377 | 9/1988 | Barger et al. | 585/323 |
| 4,781,906 | 11/1988 | Cahen et al. | 433/328 |
| 4,922,053 | 5/1990 | Waguespack et al. | 585/449 |
| 5,847,255 | 12/1998 | Ghosh et al. | 585/467 |

*Primary Examiner*—Walter D. Griffin
*Assistant Examiner*—Thuan D. Dang
*Attorney, Agent, or Firm*—Pamela S. Smith; William D. Jackson; M. Norwood Cheairs

[57] ABSTRACT

Ethylbenzene is produced by alkylation over a split load of monoclinic silicalite alkylation catalysts having different silica/alumina ratios. A feedstock containing benzene and ethylene is applied to a multi-stage alkylation reaction zone having a plurality of series-connected catalyst beds. At least one catalyst bed contains a first monoclinic silicalite catalyst having a silica/alumina ratio of at least 275. At least one other catalyst bed contains a second monoclinic silicalite catalyst having a silica/alumina ratio of less than about 275. The alkylation reaction zone is operated at temperature and pressure conditions in which the benzene is in a gaseous phase to cause gas-phase alkylation of the aromatic substrate in the presence of the monoclinic silicalite catalysts to produce an alkylation product. The alkylation product is then withdrawn from the reaction zone for separation and recovery. The use of the split load of catalyst allows a higher purity ethylbenzene product to be produced at improved efficiencies than if only one of the catalysts were used by itself.

23 Claims, 2 Drawing Sheets

GAS PHASE ALKYLATION WITH SPLIT LOAD OF CATALYST

FIELD OF THE INVENTION

This invention involves an aromatic alkylation process involving vapor phase alkylation of an aromatic substrate over silicalite aromatic alkylation catalysts to improve reactor efficiency and provide increased yields of desired alkylation products with a decrease in impurities and undesirable side reaction products.

BACKGROUND OF THE INVENTION

Aromatic conversion processes which are carried out over molecular sieve catalyst are well known in the chemical processing industry. Such aromatic conversion reactions include the alkylation of aromatic substrates such as benzene to produce alkyl aromatics such as ethylbenzene, ethyltoluene, cumene or higher aromatics and the transalkylation of polyalkyl benzenes to monoalkyl benzenes. Typically, an alkylation reactor which produces a mixture of mono- and poly- alkyl benzenes may be coupled through various separation stages to a downstream transalkylation reactor. Such alkylation and transalkylation conversion processes can be carried out in the liquid phase, in the vapor phase or under conditions in which both liquid and vapor phases are present.

Alkylation and transalkylation reactions may occur simultaneously within a single reactor. For example, where various series-connected catalyst beds are employed in an alkylation reactor as described below, it is a conventional practice to employ interstage injection of the aromatic substrate between the catalyst beds, which tends to enhance transalkylation reactions within the alkylation reactor. For example, in the ethylation of benzene with ethylene to produce ethylbenzene, the alkylation product within the reactor includes not only ethylbenzene but also polyethylbenzene, principally diethylbenzene with reduced amounts of triethylbenzene, as well as other alkylated aromatics such as cumene and butylbenzene. The interstage injection of the ethylene and benzene results not only in further alkylation reactions but also transalkylation reactions where, for example, benzene and diethylbenzene undergo transalkylation to produce ethylbenzene. Thus, even though a separate transalkylation reactor is connected downstream through a series of separation stages, it is the accepted practice to minimize polyalkylation within the alkylation reactor in order to facilitate the subsequent treatment and separation steps.

An example of vapor phase alkylation is found in U.S. Pat. No. 4,107,224 to Dwyer. Here, vapor phase ethylation of benzene over a zeolite catalyst is accomplished in a down flow reactor having four series connected catalyst beds. The output from the reactor is passed to a separation system in which ethylbenzene product is recovered, with the recycle of polyethylbenzenes to the alkylation reactor where they undergo transalkylation reactions with benzene. The Dwyer catalysts are characterized in terms of those having a constraint index within the approximate range of 1–12 and include, with the constraint index in parenthesis, ZSM-5 (8.3), ZSM-11 (8.7), ZSM-12 (2), ZSM-35 (4.5), ZSM-38 (2), and similar materials.

The molecular sieve silicalite is a well-known alkylation catalyst. For example, U.S. Pat. No. 4,520,220 to Watson et al discloses the use of silicalite catalysts having an average crystal size of less than 8 microns and a silica/alumina ratio of at least about 200 in the ethylation of an aromatic substrate such as benzene or toluene to produce ethylbenzene or ethyltoluene, respectively. As disclosed in Watson et al, the alkylation procedure can be carried out in a multi-bed alkylation reactor at temperatures ranging from about 350°–500° C. and, more desirably, about 400°–475° C., with or without a steam co-feed. The reactor conditions in Watson et al are such as to provide generally for vapor phase alkylation conditions.

Another procedure employing silicalite and involving the ethylation of benzene under vapor phase reaction conditions coupled with the recycle of polyethylbenzene containing products back to the alkylation reactor is disclosed in U.S. Pat. No. 4,922,053 to Wagnespack. Here, alkylation is carried out at temperatures generally in the range of 370° C. to about 470° C. and pressures ranging from atmospheric up to about 25 atmospheres over a catalyst such as silicalite or ZSM-5. The catalysts are described as being moisture sensitive and care is taken to prevent the presence of moisture in the reaction zone. The alkylation/transalkylation reactor comprises four series connected catalyst beds. Benzene and ethylene are introduced into the top of the reactor to the first catalyst bed coupled by recycle of a polyethylbenzene fraction to the top of the first catalyst bed as well as the interstage injection of polyethylbenzene and benzene at different points in the reactor.

Another process involving the use of a silicalite as an alkylation catalyst involves the alkylation of an alkylbenzene substrate in order to produce dialkylbenzene of a suppressed ortho isomer content. Thus, as disclosed in U.S. Pat. No. 4,489,214 to Butler et al, silicalite is employed as a catalyst in the alkylation of a monoalkylated substrate, toluene or ethylbenzene, in order to produce the corresponding dialkylbenzene, such as ethyl toluene or diethylbenzene. Specifically disclosed in Butler et al is the ethylation of toluene to produce ethyltoluene under vapor phase conditions at temperatures ranging from 350°–500° C. As disclosed in Butler, the presence of ortho ethyltoluene in the reaction product is substantially less than the thermodynamic equilibrium amount at the vapor phase reaction conditions employed.

U.S. Pat. No. 4,185,040 to Ward et al discloses an alkylation process employing a molecular sieve catalyst of low sodium content which is said to be especially useful in the production of ethylbenzene from benzene and ethylene and cumene from benzene and propylene. The $Na_2O$ content of the zeolite should be less than 0.5 wt. %. Examples of suitable zeolites include molecular sieves of the X, Y, L, B, ZSM-5, and omega crystal types, with steam stabilized hydrogen Y zeolite being preferred. Specifically disclosed is a steam stabilized ammonium Y zeolite containing about 0.2% $Na_2O$. Various catalyst shapes are disclosed in the Ward et al patent. While cylindrical extrudates may be employed, a particularly preferred catalyst shape is a so-called "trilobal" shape which is configured as something in the nature of a three leaf clover. The surface area/volume ratio of the extrudate should be within the range of 85–160 in.$^{-1}$. The alkylation process may be carried out with either upward or downward flow, the latter being preferred, and preferably under temperature and pressure conditions so that at least some liquid phase is present, at least until substantially all of the olefin alkylating agent is consumed. Ward et al states that rapid catalyst deactivation occurs under most alkylating conditions when no liquid phase is present.

U.S. Pat. No. 4,169,111 to Wight discloses an alkylation/transalkylation process for the manufacture of ethylbenzene employing crystalline aluminosilicates in the alkylation and transalkylation reactors. The catalysts in the alkylation and transalkylation reactors may be the same or different and include low sodium zeolites having silica/alumina mole ratios between 2 and 80, preferably between 4–12. Exemplary zeolites include molecular sieves of the X, Y, L, B, ZSM-5 and omega crystal types with steam stabilized Y zeolite containing about 0.2% $Na_2O$ being preferred. The alkylation reactor is operated in a downflow mode and under temperature and pressure conditions in which some liquid phase is present. The output from the alkylating reactor is cooled in a heat exchanger and supplied to a benzene separation column from which benzene is recovered overhead and recycled to the alkylation reactor. The initial higher boiling bottoms fraction from the benzene column comprising ethylbenzene and polyethylbenzene is supplied to an initial ethylbenzene column from which the ethylbenzene is recovered as the process product. The bottoms product from the ethylbenzene column is supplied to a third column which is operated to provide a substantially pure diethylbenzene overheads fraction which contains from 10 to 90%, preferably 20 to 60% of diethylbenzene. The diethylbenzene overheads fraction is recycled to the alkylation reactor while a side cut containing the remaining diethylbenzene and triethylbenzene and higher molecular weight compounds is supplied to the reactor along with benzene. The effluent from the reactor is recycled through the heat exchanger to the benzene column.

U.S. Pat. No. 4,774,377 to Barger et al discloses an alkylation/transalkylation process which, involves the use of separate alkylation and transalkylation reaction zones, with recycle of the transalkylated product to an intermediate separation zone. In the Barger process, the temperature and pressure conditions are adjusted so that the alkylation and transalkylation reactions take place in essentially the liquid phase. The transalkylation catalyst is an aluminosilicate molecular sieve including X-type, Y-type, ultrastable-Y, L-type, omega type and mordenite type zeolites with the latter being preferred. The catalyst employed in the alkylation reaction zone is a solid phosphoric acid containing material. Aluminosilicate alkylation catalysts may also be employed and water varying from 0.01 to 6 volume percent is supplied to the alkylation reaction zone. The output from the alkylation reaction zone is supplied to first and second separation zones. Water is recovered in the first separation zone. In the second separation zone, intermediate aromatic products and trialkylaromatic and heavier products are separated to provide an input to the transalkylation reaction zone having only dialkyl aromatic components, or diethylbenzene in the case of an ethylbenzene manufacturing procedure or diisopropylbenzene in the case of cumene production. A benzene substrate is also supplied to the transallylation zone for the transalkylation reaction and the output from the transalkylation zone is recycled to the first separation zone. The alkylation and transalkylation zones may be operated in downflow, upflow, or horizontal flow configurations.

EPA publication 467,007 to Butler discloses other processes having separate alkylation and transalkylation zones employing various molecular sieve catalysts and with the output from the transalkylation reactor being recycled to an intermediate separation zone. Here, a benzene separation zone, from which an ethylbenzene/polyethylbenzene fraction is recovered from the bottom with recycling of the overhead benzene fraction to the alkylation reactor is preceded by a prefractionation zone. The prefractionation zone produces an overhead benzene fraction which is recycled along with the overheads from the benzene column and a bottom fraction which comprises benzene, ethylbenzene and polyethylbenzene. Two subsequent separation zones are interposed between the benzene separation zone and the transalkylation reactor to provide for recovery of ethylbenzene as the process product and a heavier residue fraction. The polyethylbenzene fraction from the last separation zone is applied to the transalkylation reactor and the output there is applied directly to the second benzene separation column or indirectly through a separator and then to the second benzene separation column. Butler discloses that the alkylation reactor may be operated in the liquid phase with a catalyst such as zeolite-β, zeolite-Y or zeolite-Ω or in the vapor phase employing a catalyst such as silicalite or ZSM-5. In the Butler process, where vapor phase alkylation is followed by liquid phase transalkylation, substantial quantities of water may be included in the feedstream to the alkylation reactor. In this case, the feed to the transalkylation reactor may be dehydrated to lower the water content. The transalkylation catalyst may take the form of a zeolite-Y or zeolite-Ω.

SUMMARY OF THE INVENTION

In accordance with the present invention there is provided a process for the vapor-phase alkylation of an aromatic substrate. This is accomplished by introducing a feedstock comprising an aromatic substrate in a gaseous phase and an alkylation agent into contact with a first molecular sieve aromatic alkylation catalyst to produce a reaction product containing a monoalkylated aromatic substrate, polyalkylated aromatic side components and unreacted feedstock. The reaction product is then passed into contact with a second molecular sieve aromatic alkylation catalyst which is compatible with the first catalyst and which exhibits a different activity for the conversion of the alkylation agent as well as a different activity for the production of polyalkylated aromatic components to the first catalyst.

The alkylation reaction may be carried out in a reaction zone having a plurality of series-connected catalyst beds. At least one catalyst bed contains a first monoclinic silicalite catalyst having a selected silica/alumina ratio, which is preferably at least about 275, and more preferably is within the range of about 300 to 350. At least one other catalyst bed of the reaction zone contains a second monoclinic silicalite catalyst having a selected silica/alumina ratio that is less than that of the first catalyst. The second catalyst preferably has a silica/alumina ratio of less than about 275, and more preferably is within the range of about 200 to 250. The monoclinic silicalite catalysts may also be characterized by a crystal size of less than one micron. A feedstock of an aromatic substrate, such as benzene, and an alkylating agent, such as ethylene, propylene or alpha-olefin, is introduced into the multistage reaction zone and the alkylation reaction zone is operated at temperature and pressure conditions in which the aromatic substrate is in a gaseous phase to cause gas-phase alkylation of the aromatic substrate in the presence of the monoclinic silicalite catalysts to produce an alkylation product. The alkylation product is then withdrawn from the reaction zone.

In a preferred embodiment, the catalyst bed containing the first catalyst constitutes an initial stage of the reaction zone and the catalyst bed containing the second catalyst constitutes a later stage of the reaction zone. The first catalyst may also be predominant or present in a greater proportion to the second catalyst. The feedstock used may have an aromatic substrate/alkylating agent weight ratio of between about 10 to 25.

In the production of ethylbenzene or other alkylated aromatics, the alkylation product from the reaction zone may be supplied to an intermediate recovery zone for the separation and recovery of ethylbenzene from the alkylation product and for the separation and recovery of polyalkylated aromatic components. At least a portion of the polyalkylated aromatic component is supplied to a transalkylation reaction zone of the intermediate recovery zone. Benzene is supplied to the transalkylation reaction zone and the transalkylation reaction zone is operated under temperature and pressure conditions to cause disproportionation of the polyalkylated aromatic fraction to produce a disproportionation product having an enhanced ethylbenzene content and a reduced polyalkylated aromatic components content. To effect the transalkylation reaction, the transalkylation zone may contain a zeolite Y transalkylation catalyst and be operated under temperature and pressure conditions effective to maintain the feedstock in the transalkylation zone in the liquid phase.

DETAILED DESCRIPTION OF THE INVENTION

Figure 1:
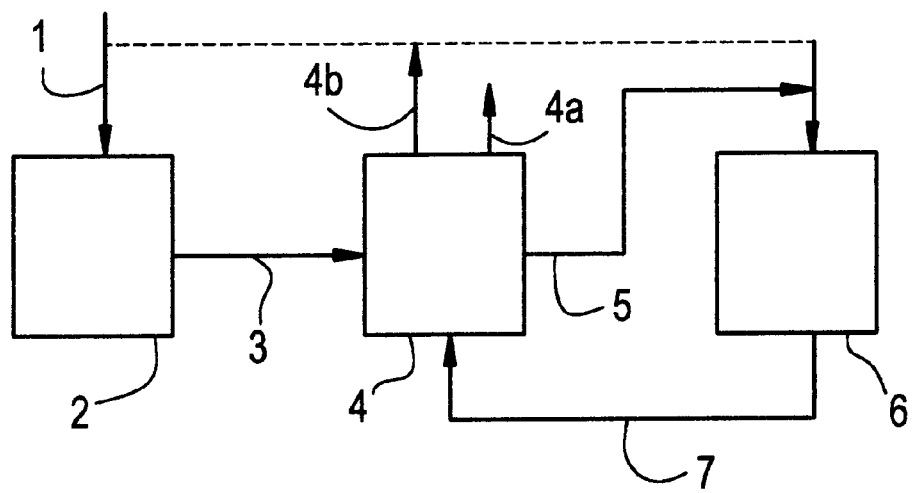
FIG. 1 is an idealized schematic block diagram of an alkylation/transalkylation process embodying the present invention.

The present invention involves the vapor-phase alkylation of benzene over compatible silicalite alkylation catalysts having different silica/alumina ratios in a multi-stage reaction zone which results in improved product quality and reaction efficiency. In the formation of ethylbenzene in vapor-phase alkylation from a feedstock of ethylene and benzene, other impurities and undesirable side products may be formed in addition to the desired ethylbenzene. These undesirable products include such compounds as xylene, cumene, n-propylbenzene and butylbenzene, as well as polyethylbenzenes, and high boiling point alkyl aromatic components, sometimes referred to as "heavies," having a boiling point at or above 185° C. As can be well understood, reduction of these impurities and side products is important. This is especially true in the case of xylene, particularly the meta and para xylenes, which have distillation points that are in close proximity to that of ethylbenzene and can make product separation and purification difficult. It should be pointed out that although the present invention has particular application to the formation of ethylbenzene through the alkylation of benzene with ethylene, the method may also be used to produce other alkylated aromatics, such as the formation of propylbenzene with the use of propylene as the alkylating agent. Other olefins may also be used as the alkylating agent.

The use of certain silicalite alkylation catalysts with higher silica/alumina ratios have demonstrated a reduced yield of these undesirable products during the production of ethylbenzene. Accompanying this, however, has been a lower overall conversion of ethylene compared to those silicalite alkylation catalysts having lower silica/alumina ratios that produce a higher percentage of impurities. As used herein, the use of "high," "higher," "low," or "lower" with reference to the silica/alumina ratio of the silicalite catalysts are comparative terms that refer only to the relative silica/alumina ratios of the silicalite catalysts as compared to one another and not to other non-silicalite catalysts that may contain silica and alumina. By combining these different catalysts in a split-load arrangement in an alkylation reactor, as is described in further detail below, a synergistic effect is achieved that results in a greater reaction efficiency and which allows a higher throughput with improved product quality.

The practice of the present invention involves the use of a multi-stage alkylation reactor having a plurality of series-connected catalyst beds filled with the alkylation catalysts. One or more of the catalyst beds is filled with a monoclinic silicalite alkylation catalyst having a high silica/alumina ratio, more specifically a silica/alumina ratio of at least about 275. Preferably, the bed or beds containing the high silica/alumina ratio catalyst are located at the initial stages of the reaction zone. In addition, one or more catalyst beds of the alkylation reactor are filled with a monoclinic silicalite catalyst having a lower silica/alumina ratio, more specifically a silica/alumina ratio of less than about 275. The lower silica/alumina ratio catalyst bed or beds preferably will be located at the later stages of the reaction zone of the reactor. Of course, the actual location of the catalyst-filled beds for the initial and later stages may vary depending whether the reactor is a top feed, bottom feed or horizontal reactor. In the examples given herein, the reactors used are top-feed reactors, with the high silica/alumina ratio catalyst beds located in the upper portion of the reactor, and the lower silica/alumina ratio catalyst bed(s) located in the lower portion. In a typical vapor-phase alkylation reactor, there may be between four to eight catalyst beds in the reactor. Preferably, there is a greater proportion of the high silica/alumina ratio catalyst used within the reaction zone. Thus, only one or two of the beds are filled with the lower silica/alumina ratio catalyst, with the remaining beds being filled with the higher silica/alumina ratio catalyst.

The silicalite employed in the present invention for both the higher and lower silica/alumina ratio catalysts has a smaller crystal size than the silicalite traditionally employed in aromatic alkylation procedures. Silicalite, as is well known in the art, is a molecular sieve catalyst which is similar to the ZSM-5 zeolites but is typically characterized by a higher silica/alumina ratio providing an aluminum/unit cell ratio of less than 1, and, in addition, is normally characterized as having a somewhat larger than average crystal size than is commonly associated with the ZSM zeolites. As is well known in the art, silicalite, which in the as-synthesized form is characterized by orthorhombic symmetry, can be converted to monoclinic symmetry by a calcination procedure as disclosed, for example, in U.S. Pat. No. 4,599,473 to DeBras et al. As described in detail in DeBras et al, "Physico-chemical characterization of pentasil type materials, I. Precursors and calcined zeolites, and II. Thermal analysis of the precursors," *Zeolites*, 1985, Vol. 5, pp. 369–383, the silicalite typically has a relatively large crystal size. Thus, at an average of less than one aluminum atom per unit cell (a silica/alumina ratio of about 200) silicalite typically has an average crystal size of perhaps 5–10 microns or more. The aforementioned U.S. Pat. No. 4,489,214 to Butler et al discloses experimental work involving the ethylation of toluene over silicalite of a crystal size greater than one micron, ranging from 1–2 microns up to 8 microns. The silicalite is further characterized in terms of a variable aluminum gradient such that the aluminum gradient is positive when going from the interior to the surface of the molecular sieve crystal. That is, the silicalite can be characterized by a core portion which is relatively aluminum deficient with an outer shell portion which is relatively aluminum rich. It is to be understood that the term "aluminum rich" is a relative term and that for silicalite even the outer shell portion of the crystallite has a low aluminum content.

Vapor-phase alkylation using the split-load of silicalite catalyst as described herein will usually be followed by a liquid phase transalkylation procedure in which the alkylation and transalkylation reactors are integrated with an intermediate recovery zone, preferably involving a plurality of separation zones operated in a manner to effectively provide feed streams to the reactors with recycle of the output from the transalkylation reactor to a benzene recovery zone downstream of the alkylation reactor. In this integrated mode of operation, the transalkylation product is applied to an initial stage of a benzene recovery zone. Subsequent separation steps are carried out in a manner to apply a split feed to the transalkylation reactor. The alkylation reactor is a multistage reaction zone containing at least three series connected catalyst beds which contain the split loads of silicalite alkylation catalysts, more preferably four or more beds are employed. As described in greater detail below, the silicalite alkylation catalysts preferably are silicalite characterized as having a high monoclinicity and a small sodium content, both in terms of sodium in the crystalline molecular sieve structure and in the binder component. The preferred catalyst used in the transalkylation reactor is a molecular sieve having a pore size greater than the pore size of the silicalite catalyst. Preferably, the transalkylation catalyst is zeolite Y. As will be described in greater detail below, the alkylation reactor is preferably operated at substantially higher temperature conditions than the transalkylation reactor. In one embodiment of the invention, the recycled output from the transalkylation reactor is passed in a heat exchange relationship with the alkylation reactor product feed to the initial benzene separation zone.

A preferred application of the invention is in a system involving a multistage alkylation reactor with a split load of catalyst with the output of the reactor coupled to a four-stage separation system, which in turn supplies a polyethylbenzene feed to a transalkylation reactor. In the embodiment of the invention described herein, parallel alkylation and transalkylation reactors are employed. This results in a preferred mode of operation in which the parallel alkylation reactors are simultaneously operated in an alkylation mode while periodically one reactor can be taken off-stream with the feedstream completely supplied to the on-stream reactor. In the embodiment illustrated and described below, two parallel reactors are employed although it is to be recognized that three or more reactors can likewise be employed in parallel. A similar configuration is employed for the transalkylation reactors. The result is that simultaneous catalyst regeneration can occur in one reactor during operation of the remaining alkylation and/or transalkylation reactors. Assuming that two parallel reactors are employed, it can be seen that this mode of operation will, for the same flow rate of feedstream, result in the operation of the reactors at two different space velocities, with the space velocity during regeneration of a reactor being about twice that with both parallel reactors in operation.

Preferably the alkylation reactor comprises at least four catalyst beds as described above. More beds can be provided, and it will sometimes be advantageous to provide at least five or six catalyst beds in the alkylation reactor. The reactor is operated so as to provide vapor phase alkylation (both the aromatic substrate and the alkylating agent are in the vapor phase) at temperatures ranging from about 630° F.–800° F. at the inlet to about 700° F.–850° F. at the outlet. The pressure may be within the range of about 250 to 450 psia with the pressure decreasing from one bed to the next as the temperature increases. By way of example, the benzene and ethylene supplied to the top of the reactor may enter the reactor at a temperature of about 740° F. and a pressure of about 430 psia. The alkylation reaction is exothermic so that the temperature progressively increases from the first to the last catalyst bed by a way of example. The interstage temperatures may increase from 750° F. for the first catalyst bed to 765° F. after the second catalyst bed to 820° F. after the third catalyst bed to a temperature of about 840° F. after the last catalyst bed.

Normally in the operation of multi-stage reaction zone of the type involved in the present invention, a benzene-ethylene mixture is introduced to the first catalyst bed at the initial stage of the reaction zone and also in between the several successive stages of catalyst beds. In the examples presented, ethylene is supplied along with benzene to the first catalyst bed located at the top or upper end of the reactor. In addition, interstage injection of ethylene and benzene is provided for between the subsequent catalyst beds. The feedstock benzene-to-ethylene weight ratio injected into the top of the alkylation reactor may be between about 18 to 22. The alkylation reactor may be operated with the benzene to ethylene weight ratio progressively decreasing along the length of the reactor because of the interstage injection of ethylene and the subsequent alkylation of the benzene to ethylbenzene and polyethylbenzenes. Benzene-to-ethylene weight ratios for the present invention may vary anywhere from between about 10–25. Due to increased efficiencies of the split-load catalyst reactor, the alkylation feedstock may have a much lower benzene-to-ethylene weight ratio than if only a single catalyst were used. The benzene-to-ethylene weight ratio for the alkylation reaction feedstock may be as low as 10–14 while still maintaining acceptable product quality and reactor efficiency.

The silicalite alkylation catalyst employed in the present invention does not require the presence of water to stabilize the catalyst, so a water or steam co-feed, as is sometimes used in connection with silicalite, is not called for in this invention. As noted above, interstage injection of ethylene is normally employed, and the interstage injection of benzene can also be provided for. The weight ratio of the benzene to the ethylene at the interstage injection points can vary from zero (no benzene injection) up to about five. The benzene in many cases will be employed in an amount less than the amount of ethylene on a weight basis. Stated otherwise, benzene can either not be injected between the catalyst beds or, if injected, can be employed in a relatively minor amount, i.e., a weight ratio of benzene to ethylene of less than one. On the other hand, the benzene/ethylene weight ratio can be as high as five. This is coupled with a somewhat lower operating temperature than would normally be the case for vapor phase alkylation. In the preferred embodiment of the invention, the temperature of the benzene stream into the top of the alkylation reactor will be in the order of 720° F. or lower. The alkylation reaction is, of course, an exothermic reaction so that the temperature will be increased progressively throughout the alkylation column.

The silicalite alkylation catalysts, both the high and low silica/alumina ratio catalysts as referred to herein, are molecular sieves from the pentasil family of high silica molecular sieves. Such pentasil molecular sieves are described, for example, in Kokotailo et al, "Pentasil Family of High Silica Crystalline Materials," Chem. Soc. Special Publ. 33, 133–139 (1980). The silicalite molecular sieve alkylation catalysts have a somewhat smaller pore size than the preferred zeolite-Y employed in the transalkylation reactor. The silicalite catalysts have an effective pore size or window within the range of 5–6 angstroms. Zeolite Y has a pore size of about 7 angstroms. The preferred silicalite catalysts have a somewhat smaller crystal size, less than one micron, than is usually the case. Preferably, the crystal size is even somewhat smaller, providing an average crystal size of about $0.5\mu$ or less, as contrasted with crystal sizes of perhaps $1-2\mu$ up to about 8 microns for similar catalysts such as disclosed in the aforementioned U.S. Pat. No. 4,489,214 to Butler et al.

Preferred silicalites for the catalysts used in the present invention are extruded with an alumina binder in a "trilobe" shape having a nominal diameter of about 1/16" and a length of the extrudate of about 1/8–1/4." As discussed below, the silicalite catalysts have a low sodium content and this is complemented in the preferred embodiment of the invention by the use of an alumina binder which is of unusually high purity and unusually large pore size as described in greater detail below. The "trilobe" cross sectional shape is something on the order of a three leaf clover. The purpose of this shape is to increase the surface area of the extruded catalyst beyond what one would expect with a normal cylindrical extrudate. The silicalite catalysts used are characterized as monoclinic silicalite. Monoclinic silicalite may be prepared as disclosed in U.S. Pat. No. 4,781,906 to Cahen et al and U.S. Pat. No. 4,772,456 to DeClippeleir et al. Preferably the catalysts will have near 100% monoclinicity) although silicalite catalysts that are 70–80% monoclinic and about 20–30% orthorhombic symmetry may be used in the preferred embodiment of the invention. The silicalite preferably is present in an amount of 75–80 wt. % with the alumina binder being present in an amount of 20–25 wt. %. The silicalite may have an alpha value of about 20–30. The "alpha value" is characterized in terms of the activity of a catalyst for cracking hexane as disclosed in U.S. Pat. Nos. 4,284,529 to Shihabi and 4,559,314 to Shihabi. The silicalite catalyst typically contains small amounts of sodium and iron.

As noted previously, the silicalite alkylation catalysts have a crystal structure characterized by an aluminum rich outer shell and an aluminum deficient interior portion when compared with the outer shell. The silicalite catalysts are dry and have no appreciable or intended water content. Specifically, the silicalite catalysts preferably contain no more than about 200 ppm sodium, preferably no more than about 100 ppm sodium, and no more than about 500 ppm iron, preferably no more than about 300 ppm iron. The alumina binder is a high purity alumina such as "catapal alumina." Preferably, the alumina binder is characterized in terms of an unusually high pore size and unusually low sodium content. As noted previously, the silicalite itself has a low sodium content in its crystalline structure. By maintaining a low sodium content in the alumina, a high portion of the catalyst sites in the silicalite structure are maintained in the active hydrogen form—that is, the low sodium content of the binder tends to minimize neutralization of the crystalline catalyst sites due to ion exchange between sodium in the binder and the acid sites in the catalyst. The alumina binder is further characterized in terms of a relatively large average pore size after the catalyst is extruded and divided into particles. Specifically, the average pore size of the binder, which can be termed the "maximum" pore size to avoid confusion with the pore size of the silicalite itself, is about 1,000 angstroms or more, preferably within the range of 1000 to 4000 angstroms. A preferred pore size range is within the range of about 1,000 to about 1,800 angstroms. This relatively large pore size binder can enhance the efficiency of the catalyst by avoiding, or at least minimizing, an alumina-diffusing mechanism as applied to the catalyst particles themselves, thus enhancing access to the silicalite molecular sieve within the catalyst particles. The pore size of the molecular sieve structure itself normally can be expected to be on the order of about 5–6 angstroms. The silicalite catalysts preferably contain only a small amount of sodium, about 70–200 ppm sodium, and contain only a small amount of iron, about 200–500 ppm. The catalyst need not contain any additional "promoter" metals incorporated during the synthesis of the catalyst.

Turning now to the drawings and referring first to FIG. 1, there is illustrated a schematic block diagram of an alkylation/transalkylation process carried out in accordance with the present invention. As shown in FIG. 1, a feed stream comprising a mixture of ethylene and benzene in a weight ratio of benzene to ethylene about 10 to 25 supplied via line 1 to an alkylation zone 2. Alkylation zone 2 comprises one or more multi-stage reactor having a plurality of series-connected catalyst beds containing the split loads of silicalite alkylation catalysts as described in greater detail below. The alkylation zone is operated at temperature and pressure conditions to maintain the alkylation reaction in the vapor phase, i.e. the aromatic substrate is in the vapor phase, and at a feed rate to provide a space velocity enhancing ethylbenzene production while retarding xylene production.

The output from the alkylation reactor is supplied via line 3 to an intermediate recovery zone 4, which provides for the separation and recovery of ethylbenzene as a product. Thus, ethylbenzene is withdrawn from zone 4 via line 4a and applied for any suitable purposes such as in the production of vinylbenzene. Recovery zone 4 normally will be characterized by a plurality of series-connected distillation columns as described below and will result in a heavy polyalkylated product stream which is supplied via line 5 to a transalkylation zone 6. Typically, benzene will also be recovered from the intermediate recovery zone via a line 4b. The benzene may be applied as indicated by the broken lines both for recycle back to the alkylation reactor and also to the transalkylation zone as may be appropriate. Within the transalkylation zone, the benzene and diethylbenzene undergo a disproportionation reaction resulting in a product of enhanced ethylbenzene content and diminished benzene and diethylbenzene content. Typically, the output from the transalkylation zone will be supplied via line 7 for recycle to the separation zone 4.

Figure 2:
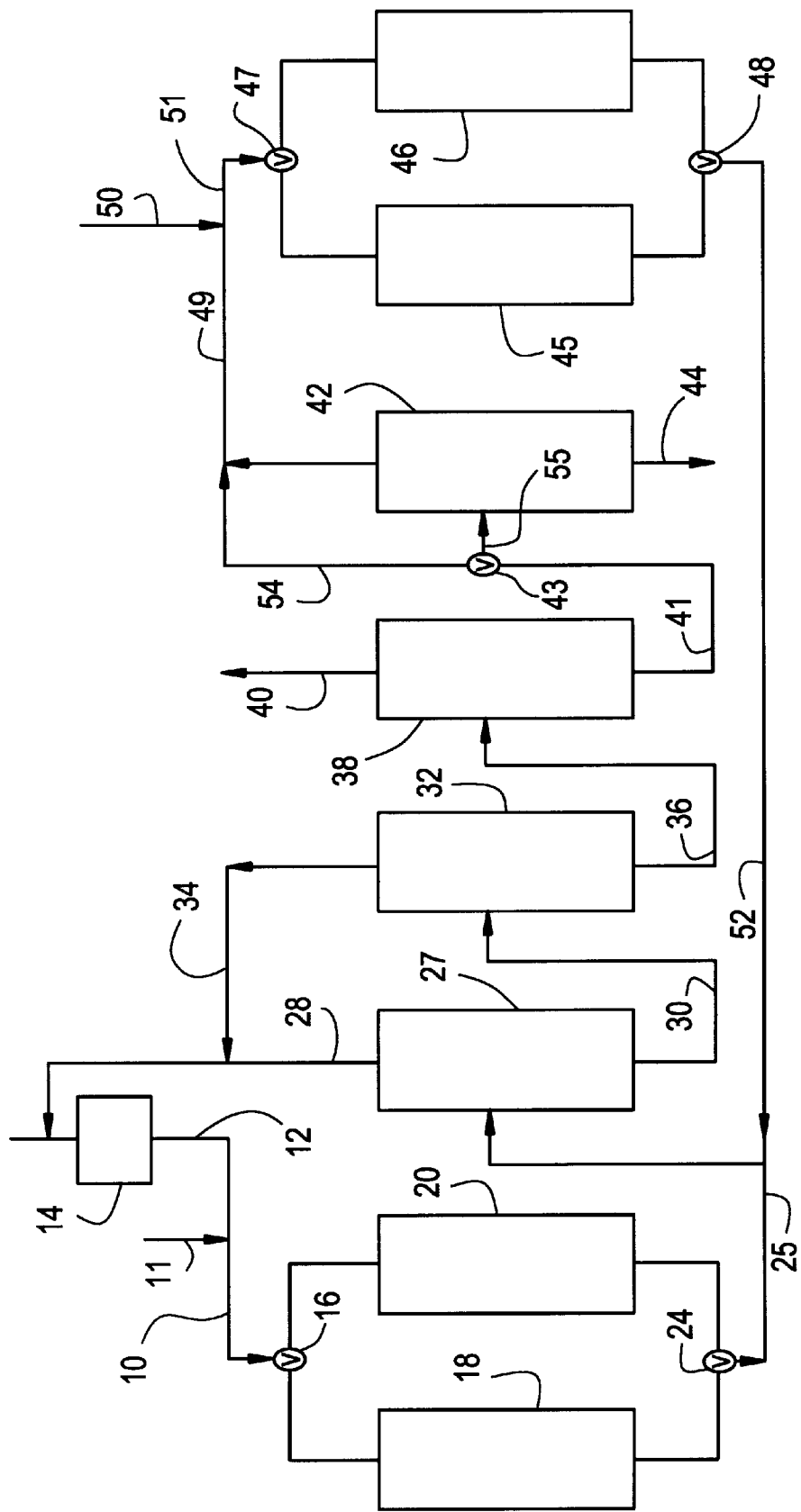
FIG. 2 is a schematic illustration of a preferred embodiment of the invention incorporating separate parallel-connected alkylation and transalkylation reactors with an intermediate multi-stage recovery zone for the separation and recycling of components.

Referring now to FIG. 2, there is illustrated in greater detail a suitable system incorporating a multi-stage intermediate recovery zone for the separation and recycling of components involved in the alkylation/transalkylation process. As shown in FIG. 2, an input feed stream is supplied by fresh ethylene through line 11 and fresh benzene through line 12. Line 12 is provided with a preheater 14 to heat the benzene stream to the desired temperature for the alkylation reaction. The feedstream is applied through a two-way, three-position valve 16 and inlet line 10 to the top of one or both parallel alkylation reaction zones 18 and 20 comprising a plurality of series connected catalyst beds each of which contains a silicalite alkylation catalyst, as described below. The reactors are operated at an average temperature, preferably within the range of 700° F.–800° F. and at pressure conditions of about 200 to 350 psia, to maintain the benzene in the gaseous phase.

In normal operation of the system depicted in FIG. 2, both reaction zones 18 and 20 will, during most of a cycle of operation, be operated in a parallel mode of operation in which they are both in service at the same time. In this case, valve 16 is configured so that the input stream in line 10 is roughly split in two to provide flow to both reactors in approximately equal amounts. Periodically, one reactor can be taken off-stream for regeneration of the catalyst. Valve 16 is configured so that all of the feedstream from line 10 can be supplied to reactor 18 while the catalyst beds in reactor 20 are regenerated and vice versa. The regeneration procedure will be described in detail below but normally will take place over a relatively short period of time relative to the operation of the reactor in parallel alkylation mode. When regeneration of the catalyst beds in reactor 20 is completed, this catalyst can then be returned on-stream, and at an appropriate point, the reactor 18 can be taken off-stream for regeneration. This mode of operation in operation of the individual catalyst beds at relatively lower space velocities for prolonged periods of time with periodic relatively short periods of operation at enhanced, relatively higher space velocities when one reactor is taken off-stream. By way of example, during normal operation of the system with both reactors 18 and 20 on-stream, the feedstream is supplied to each reactor to provide a space velocity of about 35 hr.$^{-1}$ LHSV. When reactor 20 is taken off-stream and the feed rate continues unabated, the space velocity for reactor 18 will approximately double to 70 hr.$^{-1}$ LHSV. When the regeneration of reactor 20 is completed, it is placed back on-stream, and again the flow rate space velocity for each reactor will decrease to 35 hr.$^{-1}$ until such point as reactor 18 is taken off-stream, in which the case the flow rate to reactor 20 will, of course, increase, resulting again in a transient space velocity in reactor 20 of 70 hr.$_{-1}$ LHSV.

Figure 3:
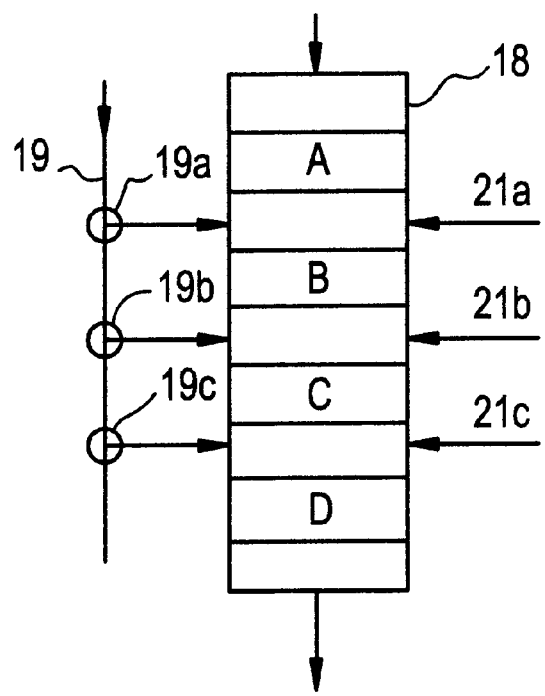
FIG. 3 is a schematic illustration of an alkylation zone comprising a plurality of series-connected catalyst beds with the interstage injection of feed components.

A preferred reactor configuration is shown in detail in FIG. 3. As illustrated there, the reactor 18 comprises four series connected catalyst beds designated as beds A, B, C and D. In the embodiment shown, the upper or initial beds A, B and C are filled with the previously described higher silica/alumina ratio silicalite catalyst, i.e. a silicalite catalyst having a silica/alumina ratio of at least 275. The bottom or last bed (bed D) is filled with a lower silica/alumina ratio silicalite catalyst, i.e. a silicalite catalyst having a silica/alumina ratio of less than 275. An ethylene feed stream is supplied via line 19 and proportionating valves 19a, 19b and 19c to provide for the appropriate interstage injection of ethylene. Benzene can also be introduced between the catalyst stages by means of secondary benzene supply lines 21a, 21b and 22b, respectively. As will be recognized, the parallel reactor 20 will be configured with similar catalyst beds containing the split load of higher and lower silica/alumina ratio silicalite catalysts and have similar manifolding, as shown in FIG. 3, with respect to reactor 18.

Returning to FIG. 2, the effluent stream from one or both of the alkylation reactors 18 and 20 is supplied through a two-way, three-position outlet valve 24 and outlet line 25 to a two-stage benzene recovery zone which comprises as the first stage a prefractionation column 27. Column 27 is operated to provide a light overhead fraction including benzene which is supplied via line 28 to the input side of heater 14 where it is mixed with benzene in line 12 and then to the alkylation reactor input line 10. A heavier liquid fraction containing benzene, ethylbenzene and polyethylbenzene is supplied via line 30 to the second stage 32 of the benzene separation zone. Stages 27 and 32 may take the form of distillation columns of any suitable type, typically, columns having from about 20–60 trays. The overheads fraction from column 32 contains the remaining benzene which is recycled via line 34 to the alkylation reactor input. Thus, line 34 corresponds to the output line 4b of FIG. 1. The heavier bottoms fraction from column 32 is supplied via line 36 to a secondary separation zone 38 for the recovery of ethylbenzene. The overheads fraction from column 38 comprises relatively pure ethylbenzene which is supplied to storage or to any suitable product destination by way of line 40, corresponding generally to output line 4a of FIG. 1. By way of example, the ethylbenzene may be used as a feedstream to a styrene plant in which styrene is produced by the dehydrogenation of ethylbenzene. The bottoms fraction containing polyethylbenzenes, heavier aromatics such as cumene and butylbenzene, and normally only a small amount of ethylbenzene is supplied through line 41 to a tertiary polyethylbenzene separation zone 42. As described below, line 41 is provided with a proportioning valve 43 which can be used to divert a portion of the bottoms fraction directly to the transalkylation reactor. The bottoms fraction of column 42 comprises a residue which can be withdrawn from the process via line 44 for further use in any suitable manner. The overhead fraction from column 42 comprises a polyalkylated aromatic component containing diethylbenzene and triethylbenzene (usually in relatively small quantities) and a minor amount of ethylbenzene is supplied to an on stream transalkylation reaction zone. Similarly as described above with respect to the alkylation reactors, parallel transalkylation reactors 45 and 46 are provided through inlet and outlet connections involving valves 47 and 48. Both of reactors 45 and 46 can be placed on stream at the same time so that both are in service in a parallel mode of operation. Alternatively, only one transalkylation reactor can be on-stream with the other undergoing regeneration operation in order to burn coke off the catalyst beds by minimizing the amount of ethylbenzene recovered from the bottom of column 38, the ethylbenzene content of the transalkylation feedstream can be kept small in order to drive the transalkylation reaction in the direction of ethylbenzene production. The polyethylbenzene fraction withdrawn overhead from column 42 is supplied through line 49 and mixed with benzene supplied via line 50. This mixture is then supplied to the on-line transalkylation reactor 45 via line 51. Preferably, the benzene feed supplied via line 50 is of relatively low water content, about 0.05 wt. % or less. Preferably, the water content is reduced to a level of about 0.02 wt. % or less and more preferably to no more than 0.01 wt. %. The transalkylation reactor is operated as described before in order to maintain the benzene and alkylated benzenes within the transalkylation reactor in the liquid phase. Typically, the alkylation reactor and the transalkylation reactor may be operated to provide an average temperature within the transalkylation reactor of about 150° F.–550° F. and an average pressure of about 600 psi. The preferred catalyst employed in the transalkylation reactor is zeolite Y having the characteristics described previously. The weight ratio of benzene to polyethylbenzene should be at least 1:1 and preferably is within the range of 1:1 to 4:1.

The output from the transalkylation reactor containing benzene, ethylbenzene and diminished amounts of polyethylbenzene is supplied via line 52 to the initial stage of the benzene recovery zone. This mode of operation is contrary to the normal mode of operation as disclosed in the aforementioned EPA 467,007 to Butler. As disclosed there, the output from the transalkylation reactor is supplied to the second stage of the benzene recovery zone, corresponding to column 32 in FIG. 2. While this mode of operation can be followed in carrying out the present invention, it is preferred, as shown in FIG. 2, for the transalkylation reactor output to be supplied to the initial stage 27 of the benzene recovery zone. This offers the advantage of having a stream with approximately the same benzene and ethylbenzene composition as the stream from the alkylation reaction.

In the mode of operation described thus far, the entire bottoms fraction from the ethylbenzene separation column 38 is applied to the tertiary separation column 42 with overhead fractions from this zone then applied to the transalkylation reactor. This mode of operation offers the advantage of relatively long cycle lengths of the catalyst in the transalkylation reactor between regeneration of the catalyst to increase the catalyst activity. Another embodiment of the invention achieves this advantage by supplying a portion of the output from the ethylbenzene separation column through valve 43 directly to the transalkylation reactor. Surprisingly, by employing vapor phase alkylation coupled with liquid phase transalkylation in accordance with the present invention, a significant quantity of the bottoms fraction from the ethylbenzene column can be sent directly to the transalkylation reactor, thus decreasing the amount of residue which is lost from the process. This mode of operation is consistent with and particularly advantageous in combination with the operation of the alkylation reactor to retard transalkylation and enhance ethylbenzene production. While applicants' invention is not to be limited by theory, it is believed that direct application of a substantial portion of the output from the ethylbenzene separation zone to the transalkylation reactor is made possible, at least in part, by the low water content in the process stream resulting from low water content introduced initially into the transalkylation reactor.

As shown in FIG. 2, a portion of the bottoms fraction from the secondary separation zone 38 bypasses column 42 and is supplied directly to the transalkylation reactor 45 via valve 43 and line 54. A second portion of the bottoms fraction from the ethylbenzene column is applied to the tertiary separation column 42 through valve 43 and line 55. The overhead fraction from column 42 is commingled with the bypass effluent in line 54 and the resulting mixture is fed to the transalkylation reactor via line 47. By bypassing the column 42 with a substantial portion of the bottoms product from column 38, the residue which is lost from the system can be reduced. Preferably in this mode of operation a substantial amount of the bottoms product from column 38 is sent directly to the transalkylation reactor, bypassing the polyethylbenzene column 42. Normally, the weight ratio of the first portion supplied via line 54 directly to the transalkylation reactor to the second portion supplied initially via line 55 to the polyethylbenzene would be within the range of about 1:2 to about 2:1. However, the relative amounts may vary more widely to be within the range of a weight ratio of the first portion to the second portion in a ratio of about 1:3 to 3:1. The invention can be further understood with reference to the following example.

EXAMPLE

Ethylbenzene production was carried out in multistage reactors, such as are shown in FIGS. 2 and 3. The catalyst beds were each filled with monoclinic silicalite catalysts designated as Catalysts A and B. The silica/alumina ratio of Catalyst A was generally between about 200 to 275. Catalyst B had a silica/alumina ratio of between about 275 to 350. Three separate trials were made with the catalysts being used separately and in combination. The reaction conditions were generally kept the same for each trial. In the trials where Catalyst A and B were each used alone, a four catalyst bed reactor was used in each case. Where the catalysts were used together, a five catalyst bed reactor was used, with Catalyst B being used in the initial or upper four catalyst beds and Catalyst A being used in the lower catalyst bed. The average ethylene conversion and xylene content were measured for each trial and are presented below in Table 1.

TABLE 1

|  | Ethylene Conversion | Xylene Content (ppm) |
| --- | --- | --- |
| Catalyst A only | 99.4% | 1070 |
| Catalyst B only | 99.15% | 819 |
| Catalyst A/B | 99.69% | 950 |

Use of the combined higher and lower silica/alumina ratio silicalite catalysts within the reaction zone of a multistage alkylation reactor can effectively lower impurity yields along with reduced formation of polyalkylated aromatics while resulting in a higher overall conversion of the alkylating agent. In the production of ethylbenzene as discussed previously, the higher silica/alumina ratio silicalite catalyst is characterized by fewer impurities and undesirable side products, principally the production of xylene, diethylbenzene, cumene, and "heavies," i.e., the post-185° C. fraction, but results in a slightly lower overall ethylene conversion (egs. from about 99.5% to about 99.2%). The lower silica/alumina ratio silicalite catalyst is characterized by a higher activity so that there is greater ethylene conversion, however, with slightly higher impurities. Thus, unreacted ethylene that has not been converted in the initial stages of the reaction zone is more readily converted with the use of the lower silica/alumina ratio silicalite catalyst in the last or later stages of the reaction zone before it exits the reactor. This occurs without any significant increase in xylene production or other impurities. The combined and synergistic effect of the higher and lower silica/alumina ratio silicalite catalysts in different stages of the reaction zone thus results in an overall improved product quality and a greater reactor efficiency. Alkylation reactions where silicalite catalyst having a higher silica/alumina ratio in the initial stages of the reaction zone may also allow a higher ethylene injection rate, which equates to a lower benzene/ethylene ratio, and a much higher throughput. As much as a 10 to 25 % increase in throughput may be achieved where the use of silicalite having a silica/alumina ratio of between 300 to 350 are used than if silicalite catalysts having a silica/alumina ratio of between about 200 to 250 were used by itself. With the combined use of the lower silica/alumina ratio catalyst in the later stages of the reaction zone, a decrease in the loss of the ethylene alkylating agent and a decrease in the impurities and polyethylbenzene residues is achieved.

Having described specific embodiments of the present invention, it will be understood that modifications thereof may be suggested to those skilled in the art, and it is intended to cover all such modifications as fall within the scope of the appended claims.

We claim:

1. A method for the vapor-phase alkylation of an aromatic substrate comprising:

providing a multi-stage alkylation reaction zone having a plurality of series-connected catalyst beds, at least one catalyst bed containing a first monoclinic silicalite catalyst having a selected silica/alumina ratio and at least one other catalyst bed containing a second monoclinic silicalite catalyst having a selected silica/alumina ratio that is less than that of the first catalyst;

introducing a feedstock of an aromatic substrate and an alkylating agent into the multistage alkylation reaction zone;

operating the multistage alkylation reaction zone at temperature and pressure conditions in which the aromatic substrate is in a gaseous phase to cause gas-phase alkylation of the aromatic substrate in the presence of the monoclinic silicalite catalysts to produce an alkylation product; and withdrawing the alkylation product from the multistage alkylation reaction zone.

2. The method of claim 1, wherein:

the aromatic substrate is benzene and the alkylating agent is an ethylating or propylating agent.

3. The method of claim 1, wherein:

the at least one catalyst bed containing the first catalyst constitutes an initial stage of the multistage alkylation reaction zone, and the at least one other catalyst bed containing the second catalyst constitutes a later stage of the multistage alkylation reaction zone.

4. The method of claim 1, wherein:

the feedstock has an aromatic substrate/alkylating agent weight ratio within the range of about 10 to 25.

5. The method of claim 1, wherein:

the first catalyst has a silica/alumina ratio of at least about 275, and the second catalyst has a silica/alumina ratio of less than about 275.

6. The method of claim 1, wherein:

the first catalyst has a silica/alumina ratio within the range of about 300 to 350, and the second catalyst has a silica/alumina ratio within the range of about 200 to 250.

7. The method of claim 1, wherein:

the multistage alkylation reaction zone comprises between 4 to 8 catalyst beds.

8. The method of claim 1, wherein:

the first and second catalyst each have a crystal size of less than one micron.

9. The method of claim 1, wherein:

the alkylation agent is an alpha-olefin.

10. The method of claim 1 wherein said aromatic substrate comprises benzene and said alkylating agent comprises ethylene.

11. A method for the vapor-phase ethylation of benzene comprising:

providing a multi-stage alkylation reaction zone having a plurality of series-connected catalyst beds, at least one catalyst bed containing a first monoclinic silicalite catalyst having a silica/alumina ratio of at least about 275 and at least one other catalyst bed containing a second monoclinic silicalite catalyst having a silica/alumina ratio of less than about 275 and less than the silica/alumina ratio of said first monoclinic silicalite catalyst;

introducing a feedstock of benzene and ethylene into the multistage alkylation reaction zone;

operating the multistage alkylation reaction zone at temperature and pressure conditions in which the benzene is in a gaseous phase to cause gas-phase ethylation of the benzene in the presence of the monoclinic silicalite catalyst to produce an alkylation product comprising a mixture of ethylbenzene and polyalkylated aromatic components including xylene and diethylbenzene; and withdrawing the alkylation product from the multistage alkylation reaction zone and separating and recovering ethylbenzene from the alkylation product.

12. The method of claim 11, wherein:

the alkylation product from the multistage alkylation reaction zone is supplied to an intermediate recovery zone for the separation and recovery of ethylbenzene from the alkylation product and for the separation and recovery of polyalkylated aromatic components, at least a portion of the polyalkylated aromatic component being supplied to a transalkylation reaction zone of the intermediate recovery zone, and wherein benzene is supplied to the transalkylation reaction zone and the transalkylation reaction zone is operated under temperature and pressure conditions to cause diproportionation of the polyalkylated aromatic fraction to produce a disproportionation product having an enhanced ethylbenzene content and a reduced polyalkylated aromatic components content.

13. The method of claim 12, wherein:

the transalkylation zone contains a zeolite Y transalkylation catalyst and is operated under temperature and pressure conditions effective to maintain the feedstock in the transalkylation zone in the liquid phase.

14. The method of claim 11, wherein:

the at least one catalyst bed containing the first catalyst constitutes an initial stage of the multistage alkylation reaction zone, and the at least one other catalyst bed containing the second catalyst constitutes a later stage of the reaction multistage alkylation zone.

15. The method of claim 11, wherein:

the feedstock has a benzene/ethylene ratio weight ratio within the range of about 10 to 25.

16. The method of claim 11, wherein:

the first catalyst has a silica/alumina ratio within the range of about 300 to 350.

17. The method of claim 11, wherein:

the second catalyst has a silica/alumina ratio within the range of about 200 to 250.

18. The method of claim 11, wherein:

the multistage alkylation reaction zone comprises between 4 to 8 catalyst beds.

19. The method of claim 11, wherein:

the first and second catalyst each have a crystal size of less than one micron.

20. A method for the vapor-phase ethylation of benzene comprising:

providing a multi-stage alkylation reaction zone having a plurality of series-connected catalyst beds, at least one catalyst bed containing a first monoclinic silicalite catalyst having a silica/alumina ratio of between about 300 to 350 and at least one other catalyst bed containing a second monoclinic silicalite catalyst having a silica/alumina ratio of less than about 200 to 250;

introducing a feedstock of benzene and ethylene in a benzene/ethylene weight ratio of between about 10 to 25 into the multistage alkylation reaction zone;

operating the alkylation multistage reaction zone at temperature and pressure conditions in which the benzene is in a gaseous phase to cause gas-phase ethylation of the benzene in the presence of the monoclinic silicalite catalysts to produce an alkylation product comprising a mixture of ethylbenzene and polyalkylated aromatic components including xylene and diethylbenzene;

withdrawing the alkylation product from the multistage alkylation reaction zone; and supplying the alkylation product to an intermediate recovery zone for the separation and recovery of ethylbenzene from the alkylation product and for the separation and recovery of polyalkylated aromatic components, at least a portion of the polyalkylated aromatic component being supplied to a transalkylation reaction zone of the intermediate recovery zone, and wherein benzene is supplied to the transalkylation reaction zone and the transalkylation reaction zone is operated under temperature and pressure conditions to cause diproportionation of the polyalkylated aromatic fraction to produce a disproportionation product having an enhanced ethylbenzene content and a reduced polyalkylated aromatic components content.

21. The method of claim 20, wherein:

the transalkylation zone contains a zeolite Y transalkylation catalyst and is operated under temperature and pressure conditions effective to maintain the feedstock in the transalkylation zone in the liquid phase.

22. The method of claim 20, wherein:

the at least one catalyst bed containing the first catalyst constitutes an initial stage of the multistage alkylation reaction zone, and the at least one other catalyst bed containing the second catalyst constitutes a later stage of the reaction zone.

23. The method of claim 20, wherein:

the multistage alkylation reaction zone comprises between 4 to 8 catalyst beds.

\* \* \* \* \*